(12) United States Patent
Helmer

(10) Patent No.: US 11,395,882 B2
(45) Date of Patent: Jul. 26, 2022

(54) DEVICE FOR ATTACHMENT TO AN INJECTION DEVICE

(71) Applicant: Sanofi-Aventis Deutschland GMBH, Frankfurt am Main (DE)

(72) Inventor: Michael Helmer, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 708 days.

(21) Appl. No.: 16/328,376

(22) PCT Filed: Aug. 18, 2017

(86) PCT No.: PCT/EP2017/070976
§ 371 (c)(1),
(2) Date: Feb. 26, 2019

(87) PCT Pub. No.: WO2018/036938
PCT Pub. Date: Mar. 1, 2018

(65) Prior Publication Data
US 2020/0078519 A1    Mar. 12, 2020

(30) Foreign Application Priority Data
Aug. 26, 2016   (EP) ..................................... 16185805

(51) Int. Cl.
*A61M 5/20*      (2006.01)
*A61M 5/24*      (2006.01)
(Continued)

(52) U.S. Cl.
CPC ............ *A61M 5/2033* (2013.01); *A61M 5/24* (2013.01); *A61M 2005/2006* (2013.01);
(Continued)

(58) Field of Classification Search
CPC ...... A61M 2005/2006; A61M 2205/14; A61M 5/2033; G16H 20/17
See application file for complete search history.

(56) References Cited

U.S. PATENT DOCUMENTS

2011/0313349 A1    12/2011  Krulevitch et al.
2014/0354998 A1*   12/2014  Bock ...................... A61M 5/31
                                                          356/445
(Continued)

FOREIGN PATENT DOCUMENTS

CN       101405738       4/2009
CN       102170929       8/2011
(Continued)

OTHER PUBLICATIONS

International Preliminary Report on Patentability in International Application No. PCT/EP2017/070976, dated Feb. 26, 2019, 9 pages.

(Continued)

*Primary Examiner* — Jenna Zhang
(74) *Attorney, Agent, or Firm* — Fish & Richardson P.C.

(57) ABSTRACT

A supplementary device configured to be releasably attached to a drug delivery device. The supplementary device comprises a housing having a channel configured to slidably receive the drug delivery device; a first alignment feature to ensure a specific alignment of the supplementary device relative to the drug delivery device and restrict rotational movement of the supplementary device around a drug delivery device; and a second alignment feature to prevent sliding movement of the supplementary device relative to the delivery device once attached thereto. The second alignment feature comprises a moveable securing member biased towards the drug delivery device, and a release member (Continued)

operable to move the securing member out of engagement with the drug delivery device.

18 Claims, 10 Drawing Sheets

(51) Int. Cl.
  *G16H 20/17* (2018.01)
  *A61M 5/31* (2006.01)
(52) U.S. Cl.
  CPC . *A61M 2005/3126* (2013.01); *A61M 2205/14* (2013.01); *A61M 2205/6036* (2013.01); *G16H 20/17* (2018.01)

(56) References Cited

U.S. PATENT DOCUMENTS

| | | | | |
|---|---|---|---|---|
| 2015/0025470 | A1* | 1/2015 | Baran | A61B 5/14532 604/187 |
| 2016/0051762 | A1* | 2/2016 | Allerdings | A61M 5/24 604/187 |

FOREIGN PATENT DOCUMENTS

| | | |
|---|---|---|
| CN | 103702699 | 4/2014 |
| CN | 104093438 | 10/2014 |
| CN | 104220114 | 12/2014 |
| CN | 104245020 | 12/2014 |
| CN | 104363940 | 2/2015 |
| CN | 105102023 | 11/2015 |
| CN | 105120929 | 12/2015 |
| CN | 105120930 | 12/2015 |
| CN | 105339026 | 2/2016 |
| JP | 2012-519025 | 8/2012 |
| JP | 2015-509769 | 4/2015 |
| JP | 2015-509770 | 4/2015 |
| JP | 2016-515453 | 5/2016 |
| WO | WO 2007/107564 | 9/2007 |
| WO | WO 2010/037828 | 4/2010 |
| WO | WO 2010/098927 | 9/2010 |
| WO | WO 2013/004844 | 1/2013 |
| WO | WO 2013/076026 | 5/2013 |
| WO | WO 2013/120773 | 8/2013 |
| WO | WO 2013/120774 | 8/2013 |
| WO | WO 2013/120776 | 8/2013 |
| WO | WO 2014/161952 | 10/2014 |
| WO | WO 2014/173771 | 10/2014 |
| WO | WO 2014/173773 | 10/2014 |
| WO | WO 2014/198799 | 12/2014 |
| WO | WO 2016/118736 | 7/2016 |

OTHER PUBLICATIONS

International Search Report and Written Opinion in International Application No. PCT/EP2017/070976, dated Nov. 23, 2017, 14 pages.

* cited by examiner

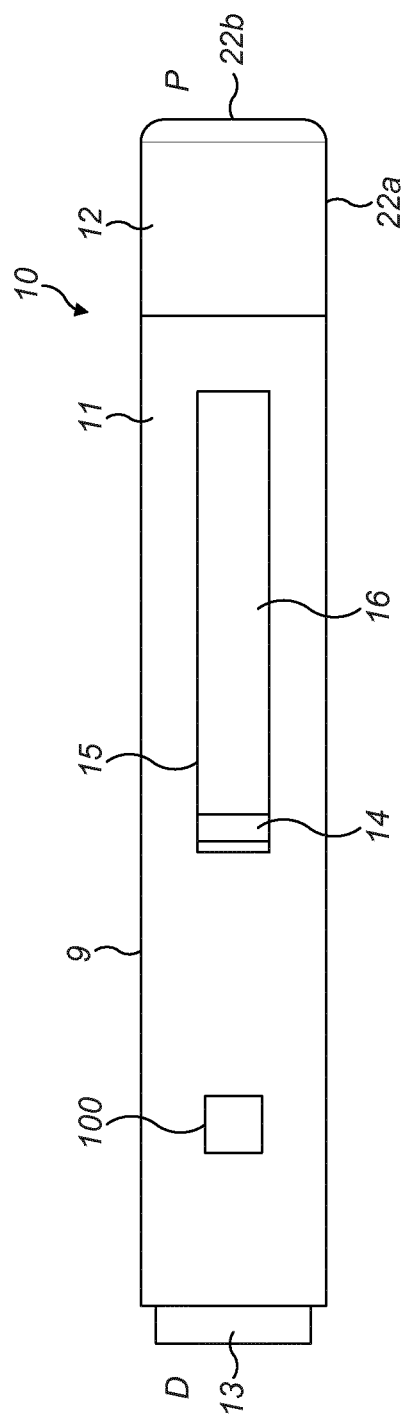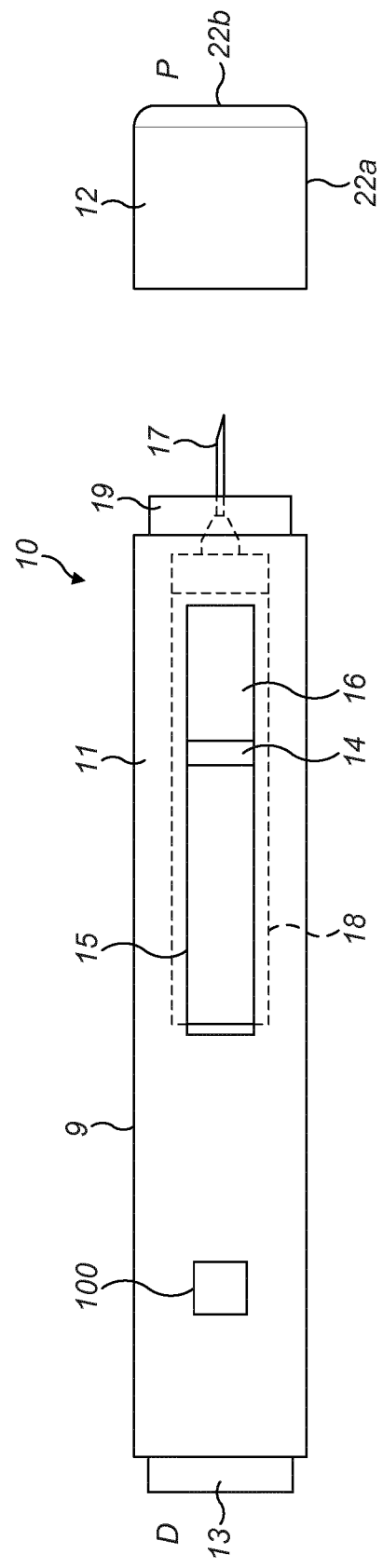
FIG. 1A
FIG. 1B

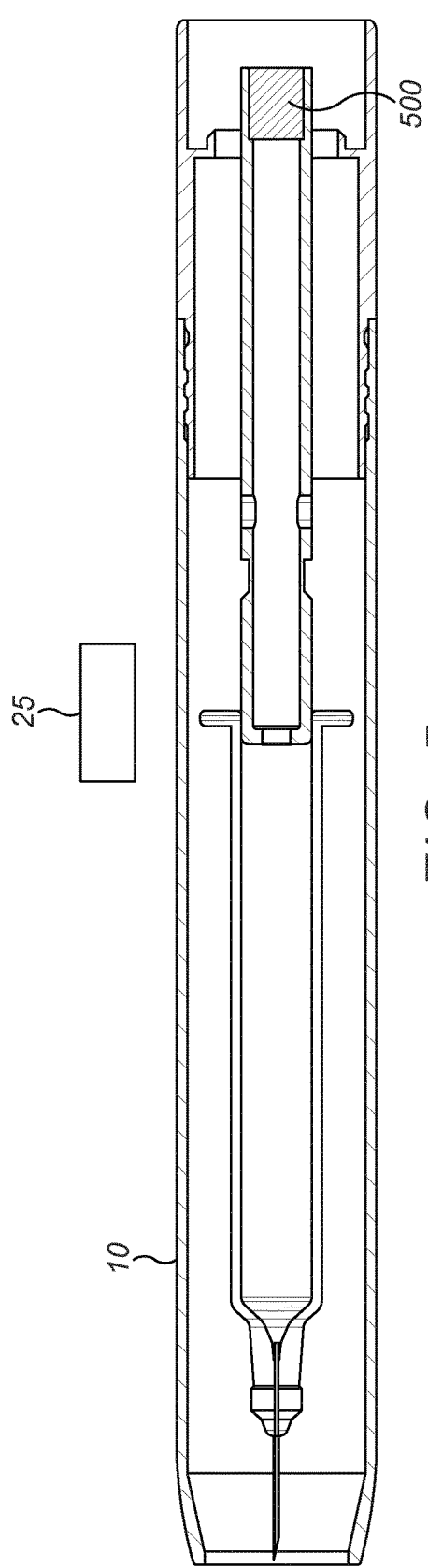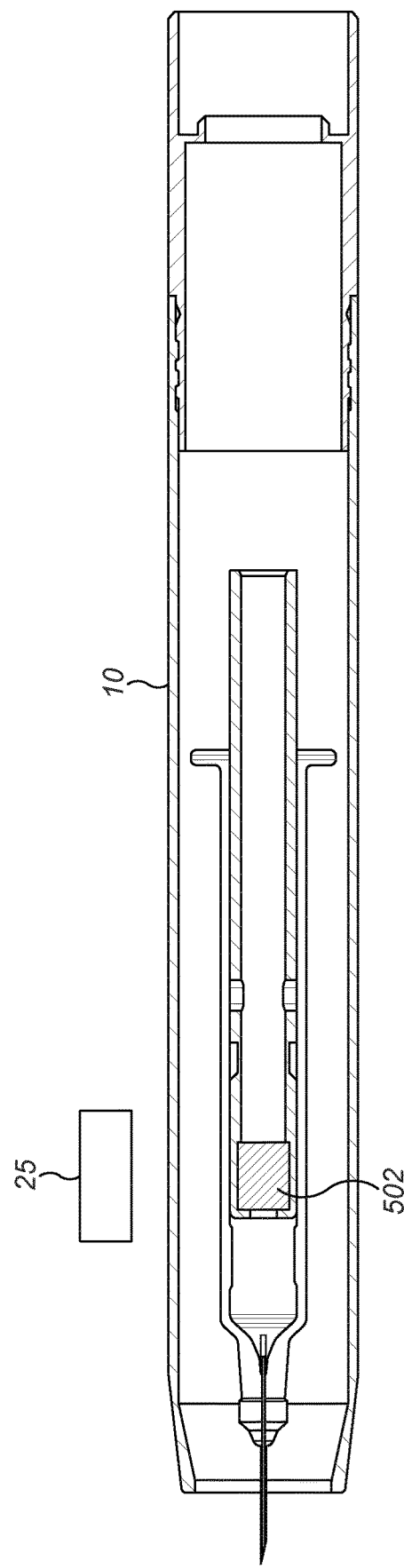

DEVICE FOR ATTACHMENT TO AN INJECTION DEVICE

CROSS REFERENCE TO RELATED APPLICATIONS

The present application is the national stage entry of International Patent Application No. PCT/EP2017/070976, filed on Aug. 18, 2017, and claims priority to EP Application No. 16185805.5, filed on Aug. 26, 2016, the entire contents of each of which are incorporated herein by reference.

TECHNICAL FIELD

The present disclosure relates to a device configured to retain an injection device or syringe and to remind a user when a medicament injection is due.

BACKGROUND

A variety of diseases exists that require regular treatment by injection of a medicament. Such injection can be performed by using injection devices, which are applied either by medical personnel or by patients themselves.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button and/or the needle cover (sleeve triggered devices)/plunger that has to be continuously pressed by the user during the injection. There are numerous disadvantages for the user from this approach. If the user stops pressing the button/plunger, then the injection will also stop. This means that the user can deliver an underdose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, allergies, hormone therapies, anticoagulants etc. Auto-injector devices can be used to deliver a single dose of a particular life-saving drug. For example they are often prescribed to people who are at risk for anaphylaxis. They are also often used in the military to protect personnel from chemical warfare agents. Alternatively, auto-injectors are used to administer medicaments according to a prescribed therapeutic schedule for people suffering from Multiple Sclerosis, Rheumatroid Arthritis, Anemia, for example.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Forces required of the user/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

Auto-injectors may be disposable or single use devices which may only be used to deliver one dose of medicament and which have to be disposed of after use. Other types of auto-injectors may be reusable. Usually they are arranged to allow a user to load and unload a standard syringe. The reusable auto-injector may be used to perform multiple parenteral drug deliveries, whereas the syringe is disposed after having been spent and unloaded from the auto-injector. The syringe may be packaged with additional parts to provide additional functionality.

In a typical scenario a disease can be treated by patients themselves by injection of medicament doses using an auto-injector, for example on a daily, weekly, bi-weekly, or monthly basis.

SUMMARY

The present disclosure describes a re-usable add-on device suitable for use with one shot auto-injectors and which may record the injection history, monitor the dose administration and aid the patient in performing the injection correctly and on time.

The correct administration of drugs and its termination is important for the safety and efficacy of the drug (pharmacovigilance). Failures in administration through the user can be minimized by monitoring of the injection device and the application time.

Typical patient failures are:

1. The user may forget the correct day of maturity for their next injection. This is particularly the case for medication intervals longer than a day, e.g. twice a week, every, second day, bi-weekly, or therapy specific intervals such as 1 st week twice, 2nd week every 2nd day, as of third week 2, 2, 3-interval, e.g.

2. The user may let too much time pass between removing the auto injector cap and performing the injection, resulting in needle clogging and/or device stalling.

3. The user does not carry out the holding time (also known as "dwell time") after the end of injection.

A first aspect of the disclosure provides a supplementary device configured to be releasably attached to a drug delivery device, the supplementary device comprising a housing having a channel configured to slidably receive the drug delivery device, a first alignment feature to ensure a specific alignment of the supplementary device relative to the drug delivery device and restrict rotational movement of the supplementary device around a drug delivery device, a second alignment feature to prevent sliding movement of the supplementary device relative to the delivery device once attached thereto, wherein the second alignment feature comprises a moveable securing member biased towards the drug delivery device, and a release member operable to move the securing member out of engagement with the drug delivery device.

The first alignment feature may be configured to engage with a cooperating feature of the drug delivery device and may permit sliding movement of the drug delivery device within the channel.

The first alignment feature may comprise a slot formed in the housing which is configured to receive a projection formed on the drug delivery device.

The securing member may comprise a boss configured to be received in a recess formed in the drug delivery device.

The supplementary device may further comprise a biasing member configured to bias the securing member towards the drug delivery device.

The securing member may be integrally formed with the housing.

The release member may comprise a release lever rotatable between a rest position in which the securing member is permitted to engage the drug delivery device, and a release position in which the securing member is moved out of engagement with the drug delivery device.

The release lever may comprise a shaft and a radial projection from the shaft configured to engage with the securing member.

The supplementary device may further comprise a locking mechanism including an actuator moveable between a locked position and an unlocked position, wherein the locking mechanism may be operable to releasably lock the supplementary device to a drug delivery device.

The actuator may include a visual indicator to indicate when the actuator is in one of the locked or unlocked positions.

The actuator may be configured to render the supplementary device operable when in the locked position and inoperable when in the unlocked position.

The actuator may be configured to trigger a function of the supplementary device when moved to the locked and/or unlocked position.

The supplementary device may further comprise a third alignment feature comprising opposing flat reference surfaces formed on the inner wall of the channel of the housing.

The flat reference surfaces may be equally spaced from a centre line extending through the supplementary device. Each reference surface may be angled by the same degree away either side of a vertical line extending through the supplementary device.

A second aspect of the disclosure provides a system comprising the supplementary device as described above and a drug delivery device, wherein the drug delivery device comprises corresponding alignment features configured to respectively cooperate with the first and second alignment features of the supplementary device.

The drug delivery device may comprise a reservoir of liquid medicament.

A third aspect of the disclosure provides a method of operating a supplementary device configured to be releasably attached to a drug delivery device, the supplementary device comprising a housing having a channel, a first alignment feature, and a second alignment feature comprising a moveable securing member biased towards the drug delivery device and a release member, the method comprising sliding a drug delivery device into the channel in the housing, releasably attaching the supplementary device to the drug delivery device, the first alignment feature engaging with the drug delivery device to ensure a specific alignment of the supplementary device relative to the drug delivery device and restrict rotational movement of the supplementary device around a drug delivery device, the second alignment feature engaging with the drug delivery device to prevent sliding movement of the supplementary device relative to the delivery device once attached thereto, and operating the release member after use of the drug delivery device to move the securing member out of engagement with the drug delivery device.

The supplementary device may comprise a non-contact sensor configured to output signals indicative of the position of a moveable component within the drug delivery device, and a processor configured to receive the signals output from the non-contact sensor and to determine based on the signals whether the drug delivery device is in a pre-activation state or a post-activation state.

This may allow the supplementary device to notify a user regarding the operational state of the device and the supplementary device may do this more clearly and effectively than the drug delivery device is able to do. Using a non-contact sensor allows the supplementary device to monitor the drug delivery device without any increase in friction on the mechanical components of the drug delivery device. The moveable component within the drug delivery device is already present in the design of the mechanism of the drug delivery device and therefore no significant modifications to the way in which this mechanism operates are required to implement this aspect of the present disclosure. Thus the increases in the complexity of manufacture of the drug delivery device are minor.

The non-contact sensor may be a capacitive sensor. Components of the capacitive sensor may be arranged within the supplementary device such that the attached drug delivery device forms at least a part of a dielectric layer of the capacitive sensor. The capacitive sensor may comprise opposing sets of at least one electrically conductive plate.

The non-contact sensor may be a Hall sensor configured to measure a magnetic field produced by the moveable component within the drug delivery device. The device may additionally include an AMR (Anisotropic magnetoresistance) sensor.

Upon determining that the drug delivery device has changed from a pre-activation state to a post-activation state, the processor may be configured to cause an indication to be output which informs a user regarding a dwell time of the drug delivery device. The supplementary device may further comprise a display unit. Causing an indication to be output may comprises causing one or more graphical elements to be displayed on the display unit, the graphical elements communicating a progress of the dwell time. The capacitive sensor may detect movement of a plunger spring to enable an entire drug delivery process, such as an injection process, to be monitored. A hall sensor may be provided to detect stalling of the delivery mechanism, such as the spring. The capacitive sensor may be able to detect an end-stop position of the drug delivery mechanism.

This may be advantageous as it may assist the user in using the drug delivery device correctly and in particular reduces the risk of the user performing an underdose by removing the needle of the drug delivery device too soon after injection of the medicament.

The supplementary device may further comprise at least one memory. The processor may be configured to cause information relating to a last performed injection operation to be stored in the memory upon determining that the drug delivery device has changed from a pre-activation state to a post-activation state. The information may comprise at least a time stamp associated with the last performed injection operation.

The information may further comprise a medicament dose amount and/or a medicament type.

Storing this information electronically may allow it to be communicated easily to other devices and people, such as the user's doctor. It may also allow the user to have greater oversight and control of their medication regime.

The processor may have access to or may be configured to calculate a time of next injection and may be further configured to produce a reminder signal when the time of next injection occurs.

The processor may have access to or may be configured to calculate a medical regimen associated with a user of the supplementary device. The medical regimen may comprise at least a series of times at which an injection operation is due to be performed. The processor may be configured to cause a reminder signal to be produced when a next injection operation is due according to the medical regimen.

Producing an automatic reminder signal may be advantageous for ensuring user compliance with their medical regimen, particularly where the user's medical regimen might mean there are many days between doses.

The supplementary device may further comprise a wireless unit for transmitting data to one or more external devices. The supplementary device may be further configured to send the reminder signal to the one or more external devices. For example, the stored information could be transmitted to the user's computer or smart phone wirelessly, for example over a Bluetooth connection.

The supplementary device may further comprise an optical sensor configured to read information visible on a housing of the injection device, the information identifying a medicament contained in the drug delivery device. This may be advantageous as it may allow the supplementary device to check the type and concentration of the medication in the drug delivery device before injection. The supplementary device may warn the user if the type or concentration of medication in the attached drug delivery device is incorrect.

The supplementary device may further comprise an outer needle cap sensor configured to output signals indicative of whether an outer needle cap is attached to the drug delivery device. The processor may be configured to receive the signals output from the outer needle cap sensor and to determine whether the outer needle cap is attached or not attached. If the processor determines that the drug delivery device is in a post-activation state and that the outer needle cap is not attached then, after a predetermined time, the processor may be configured to cause an alarm signal to be output. Causing an alarm signal to be output may comprise causing the supplementary device to emit one or more sounds and/or to display one or more indications on a display unit of the supplementary device.

This feature may help to avoid needle clogging which can occur if the drug delivery device is stored without the outer needle cap attached. The signal indicative of whether the outer needle cap is attached may also be sent to a user's smart phone or other portable device, so that they can be notified of the problem, even if they are not located near to the drug delivery device. The removal of the outer needle cap can also be used as a trigger. The removal of the outer needle cap may trigger the supplementary device to power on and to begin its monitoring processes. Therefore the user does not need to perform any additional operations to begin using the supplementary device. This greatly simplifies use of the supplementary device for a user. Similarly, the replacement of the outer needle cap may trigger the supplementary device to turn off, thus saving power.

The drug delivery device may be a powered auto-injector.

Another aspect of the disclosure may provide a system comprising the supplementary device as defined above and a drug delivery device. The drug delivery device may be a powered auto-injector. A dispensing mechanism of the powered auto-injector may be powered by a pre-compressed spring.

The drug delivery device may include a cartridge, syringe or other reservoir of liquid medicament.

BRIEF DESCRIPTION OF THE DRAWINGS

Embodiments of the present invention will now be described, by way of example only, with reference to the following figures, in which:

FIG. 1A illustrates a side view of an injection device;

FIG. 1B illustrates a side view of the injection device of FIG. 1A with a cap detached;

FIGS. 5a and 5b are cutaway illustrations of an injection device showing the possible position of internal magnets and sensors for use in sensing of the status of the injection device;

DETAILED DESCRIPTION

Figure 2:
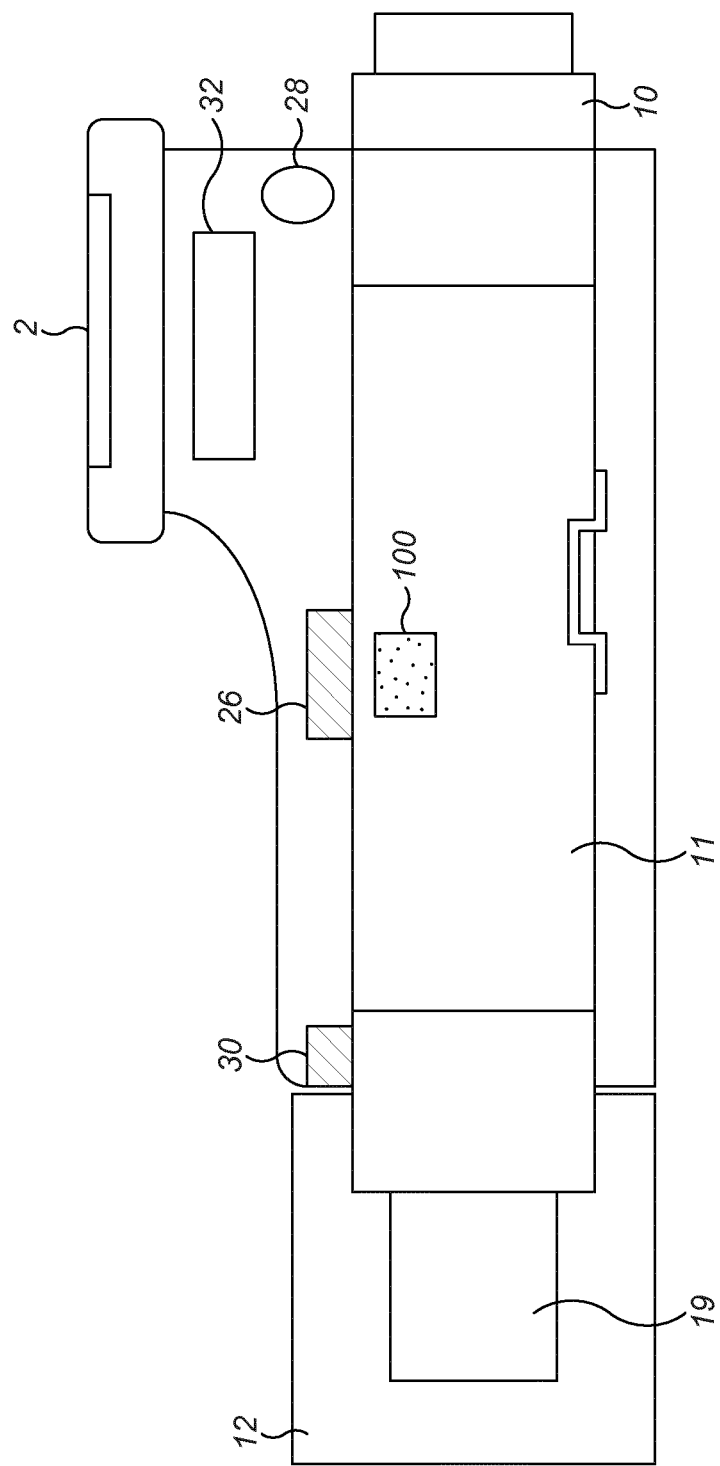
FIG. 2 is a schematic illustration of a supplementary device releasably attached to the injection device of FIGS. 1A and 1B, according to an aspect of the present disclosure.

In the following, embodiments of the present disclosure will be described with reference to an auto-injector. The present disclosure is however not limited to such application and may equally well be deployed with injection devices that eject other medicaments, or with other types of drug delivery devices, such as syringes, pre-filled syringes, needleless injectors and inhalers.

An injection device 10 according to embodiments will now be described with reference to FIGS. 1A and 1B. In some embodiments, the injection device 10 is a single use auto-injector 10. The auto-injector 10 has a proximal end P and a distal end D. The proximal end P is directed towards the injection site of a patient during an injection while the distal end D is directed away from the injection site.

The auto-injector 10 comprises a body 9 and a cap 12 (also referred to herein as the outer needle cap or ONC 12).

The body 9 comprises an outer housing 11. The outer housing 11 is an elongate tube. The outer housing 11 includes a cartridge holder or syringe holder (not shown) which supports a cartridge or syringe 18 containing liquid medicament 16. Hereafter the description shall refer to a cartridge 18, which is supported by a cartridge holder (not shown). The cartridge 18 is shown in broken lines in FIG. 1B.

The outer housing 11 also houses a dispense mechanism (not shown) for causing dispensing of the medicament 16 during injection.

A hollow needle 17 fluidly communicates with an interior volume of the cartridge 18 and serves as a conduit for liquid medicament 16 during injection. The needle 17 and the cartridge 18 are in a fixed position relative to each other and to the body 9. A stopper, plunger, piston or bung 14 is moveable within the cartridge 18 to as to expel medicament contained within the cartridge 18 through the needle 17 under action of the dispense mechanism.

The dispense mechanism is mechanically coupled to the piston 14 of cartridge 18. The dispense mechanism is configured to move the piston axially along the cartridge 18 in a proximal direction to dispense medicament 16 through the needle 17. The dispense mechanism includes components that cooperate to apply a force to the piston 14 in response to an actuation input provided by a user. Here, the actuation input that triggers application of a force to the piston 14 is received by way of a dose dispense button 13 that is located at the distal end of the auto-injector 10. The dispense mechanism is mechanically coupled to the dispense button 13. In alternative configurations of auto-injector envisaged within the scope of the present disclosure, alternative actuation inputs may be provided to trigger the dispense mechanism. For example, the dispense mechanism may include a sleeve-triggered actuator.

The body 9 also comprises a cap support 19 at the proximal end of the outer housing 11. The cap support is concentric with the outer housing 11 and may have a smaller diameter. The cap support 19 extends from the proximal end of the housing 11. The ONC 12 is received over the cap support 19 to close the proximal end of the body 9 and to cover the needle 17. The ONC 12 comprises a cylindrical wall 22a and an end wall 22b. With the ONC 12 located on the body 9, as shown in FIG. 1A, an internal surface of the cylindrical wall 22a abuts an external surface of the cap support 19 in tightly abutting relation so that the ONC 12 is retained thereon in an attached position.

To inject the medicament 16, the ONC 12 is removed from the device 10 by the user, resulting in the arrangement shown in FIG. 1B. Next, the proximal end of the auto-injector 10 is placed against an injection site of a patient, which may be the user or another person. The user then actuates the dispense button 13. This causes the dispense mechanism to force the piston 14 to expel medicament from the cartridge 18 through the needle 17 into the injection site of the patient.

The cartridge 18 is transparent and a window 15 is provided in the housing 11 coincident with the cartridge 18 so that the medicament 16 contained within the cartridge 18 is visible. A user of the auto-injector is thereby able by inspection to determine whether the entire quantity of medicament 16 has been ejected from the cartridge 18 during the injection.

A label is provided on the housing 11. The label includes information 100 about the medicament included within the injection device 10, including information identifying the medicament. The information 100 identifying the medicament may be in the form of text. The information 100 identifying the medicament may also be in the form of a colour. The information 100 identifying the medicament may also be encoded into a barcode, QR code or the like. The information 100 identifying the medicament may also be in the form of a black and white pattern, a colour pattern or shading.

FIG. 2 is a schematic illustration of an embodiment of a supplementary device 2 to be releasably attached to injection device 10 of FIG. 1. The features for accurately securing and locating the supplementary device 2 in place on the injection device 10 are omitted from FIGS. 2 to 7 for ease of illustration of the other functional features of the supplementary device 2. Such securing and locating features are described hereafter with reference to FIGS. 8 to 12. Supplementary device 2 comprises a housing 20 configured to embrace the housing 11 of injection device 10 of FIG. 1, so that the injection device 10 is at least partially retained within the supplementary device 2, but is nevertheless removable from the supplementary device 2, for instance when injection device 10 is empty and has to be replaced. The injection device 10 and supplementary device 2 may comprise co-operating alignment features (described in more detail hereafter) to ensure that the supplementary device 2 is correctly orientated and positioned with respect to the injection device 10.

Information is displayed via display unit 21 (shown in FIG. 3) of supplementary device 2. The display unit may be a touch sensitive screen. The supplementary device 2 may also comprise at least one hardware input (not shown) such as a push button. The supplementary device 2 has an outer needle cap (ONC) sensor 30. The ONC sensor may be any suitable form of proximity sensor which allows the supplementary device 2 to determine whether the ONC 12 is attached to the injection device 10 or not. The supplementary device 2 also comprises an optical sensor 26 for reading the information 100 identifying the medicament. The information 100 identifying the medicament may be the colour of the housing 11 of the injection device, or the colour of an area of the housing or a label affixed to the housing. In these embodiments, the optical sensor 26 may be a simple photometer configured to detect the colour. In some other embodiments, the information 100 identifying the medicament may be a QR code, or other similar encoded information and the optical sensor 26 may be a camera or QR reader.

The processor 24 may be configured to check the information 100 read by the optical sensor 26 against pre-stored information in order to verify that the user is injecting the correct medicament. If the processor 24 does not recognise the information 100 or recognises the information 100 as indicating a different medicament to that which the user should be receiving at that time, then the supplementary device 2 may produce an alarm signal. The alarm signal may comprise words or graphics displayed on the display unit 21. Alternatively, or in addition, the supplementary device 2 may send an alarm signal to the external device.

The supplementary device 2 comprises a battery 32 to power the other components. The supplementary device 2 comprises a wireless communication module 28 for communicating information with an external device. In some embodiments, the wireless communication module 28 is a Bluetooth communication module 28.

Figure 3:
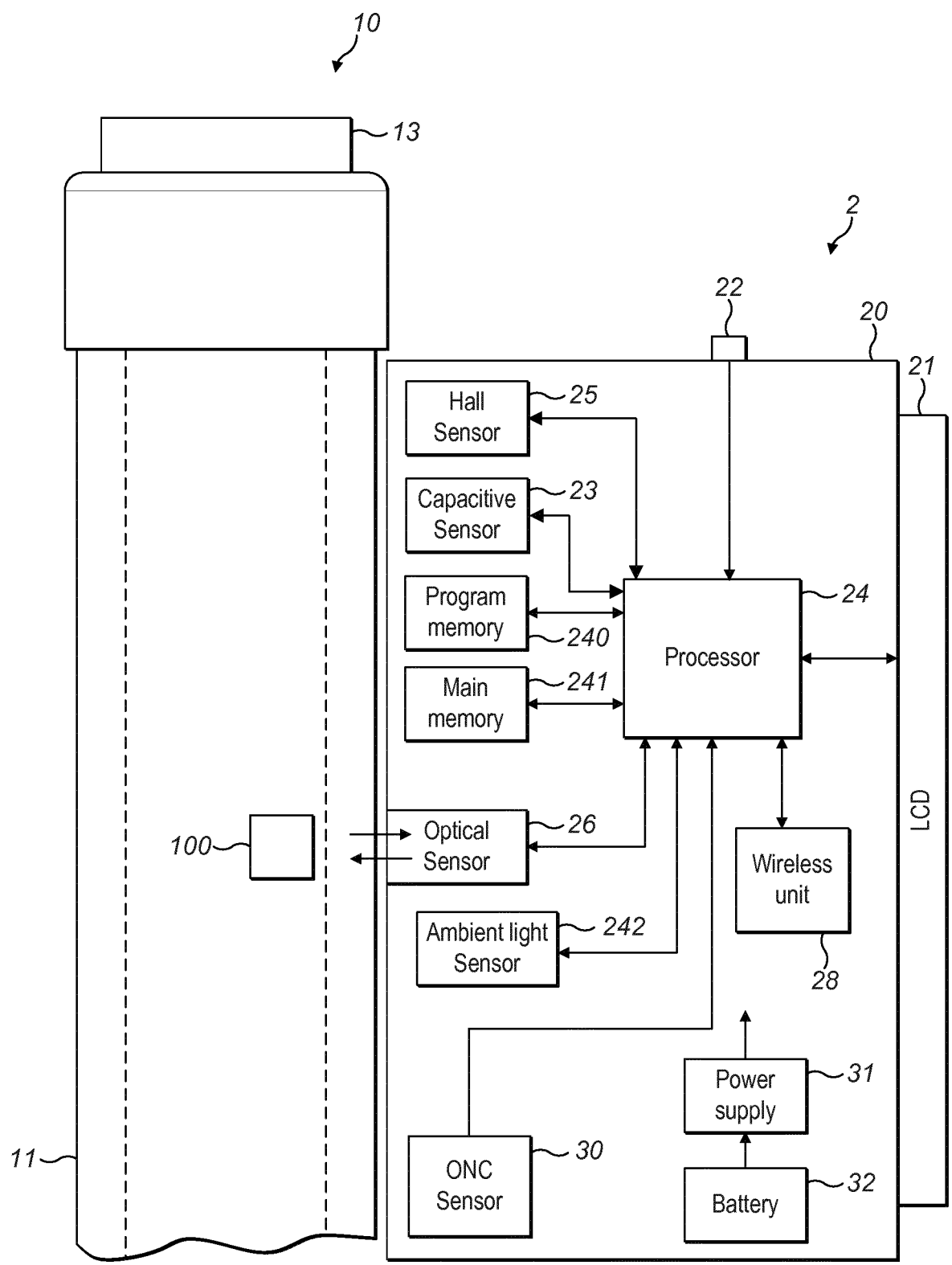
FIG. 3 is a schematic view of a supplementary device attached to an injection device showing components of the supplementary device.

FIG. 3 shows a schematic view of the supplementary device 2 of FIG. 2 in a state where it is attached to injection device 10 of FIG. 1.

A plurality of components are contained within the housing 20 of supplementary device 2. These are controlled by a processor 24, which may for instance be a microprocessor, a Digital Signal Processor (DSP), Application Specific Integrated Circuit (ASIC), Field Programmable Gate Array (FPGA) or the like. Processor 24 executes program code (e.g. software or firmware) stored in a program memory 240, and uses a main memory 241, for instance to store intermediate results. Main memory 241 may also be used to store a logbook on performed ejections/injections. Program memory 240 may for instance be a Read-Only Memory (ROM), and main memory may for instance be a Random Access Memory (RAM).

Supplementary device 2 may optionally further comprises at least one input transducer, illustrated schematically as a button 22. These input transducer 22 allows a user to turn on/off supplementary device 2, to trigger actions (for instance to cause establishment of a connection to or a pairing with another device, and/or to trigger transmission of information from supplementary device 2 to another device), or to confirm something. In some other embodiments, the supplementary device 2 is automatically turned on/off via the ONC sensor 30.

Processor 24 controls a display unit 21, which is presently embodied as a Liquid Crystal Display (LCD). Display unit 21 is used to display information to a user of supplementary device 2, for instance on present settings of injection device 1, or on a next injection to be given. Display unit 21 may also be embodied as a touch-screen display, for instance to receive user input.

Processor 24 also controls a Capacitive Sensor 23 and/or a Hall Sensor 25. In some embodiments, the supplementary device 2 comprises only the capacitive sensor 23 while in some other embodiments the supplementary device 2 comprises only the Hall sensor 25. In some further embodiments, the supplementary device 2 comprises both the capacitive sensor 23 and the hall sensor 25 where one may act as a redundant/back-up system for the other. These sensors 23, 25 are configured to output signals indicative of the positions of one or more components within the injection device 10. These sensors 23, 25 may collectively be referred to as non-contact sensors, since they are able to sense the absolute position and movement of components within the attached injection device 10 without contact between the sensors 23, 25 and any of the components sensed. It will therefore be appreciated that the position of these sensors 23, 25 relative to the injection device 10 is important for correct and accurate operation of the supplementary device 2. The processor 24 receives these signals and infers an operational state of the injection device 10 and causes information regarding the timing of the operation of the injection device 10 to be recorded in the main memory 241 and/or transmitted to an external device via the wireless unit 28. The operation of these sensors is described in greater detail with respect to FIGS. 4 and 5.

Processor 24 further controls an optical sensor 26 that is configured to determine an optical property of the housing 11 of injection device 1, for example a colour or a shading or a more complex pattern, such as a QR code. The optical property may only be present in a specific portion of housing 11, for example on a label affixed to the housing 11. Information on the colour/pattern is then provided to processor 24, which may then determine the type of injection device 10 and/or the type of medicament contained in injection device 10. The optical sensor 26 may be a camera unit, and an image of the housing 11 may then be provided to processor 24 to determine the colour of the housing, sleeve or medicament container by way of image processing. Further, one or more light sources may be provided to improve reading of optical sensor 26. The light source may provide light of a certain wavelength or spectrum to improve colour detection by optical sensor 26. The light source may be arranged in such a way that unwanted reflections, for example due to the curvature of the housing 11, are avoided or reduced. In an example embodiment, the optical sensor 26 may be a camera unit configured to detect a code 100 (for instance a bar code, which may for instance be a one- or two-dimensional bar code) related to the injection device and/or the medicament contained therein. This code 100 may for instance be located on the housing 11 or on a medicament container contained in injection device 10, to name but a few examples. This code 100 may for instance indicate a type of the injection device and/or the medicament, and/or further properties (for instance an expiration date). This code 100 may be a QR code 100. The QR code is in general black and white and thus no colour detection is required on the part of the optical sensor 26. This allows the optical sensor 26 to be simple and cheap to manufacture.

Processor 24 controls a wireless unit 28, which is configured to transmit and/or receive information to/from another device in a wireless fashion. Such transmission may for instance be based on radio transmission or optical transmission. In some embodiments, the wireless unit 28 is a Bluetooth transceiver. Alternatively, wireless unit 28 may be substituted or complemented by a wired unit configured to transmit and/or receive information to/from another device in a wire-bound fashion, for instance via a cable or fibre connection. When data is transmitted, the units of the data (values) transferred may be explicitly or implicitly defined. For instance, in case of an insulin dose, always International Units (IU) may be used, or otherwise, the used unit may be transferred explicitly, for instance in coded form. The transmitted data may also include a time stamp associated with an injection.

Processor 24 receives an input from an ONC sensor 30, which is operable to detect whether the outer needle cap 12 is present, i.e. to detect whether the outer needle cap 12 is coupled to the injection device 1. A battery 32 powers the processor 24 and other components by way of a power supply 31. The removal of the ONC 12 is detected by the ONC sensor 30 and can be used as a wake-up or switch on trigger. Thus the supplementary device may automatically turn on and begin its monitoring processes when the ONC 12 is removed. Similarly, when the ONC 12 is replaced the supplementary device may automatically power off, thus saving battery power.

The supplementary device 2 of FIG. 3 is thus capable of determining information related to a condition and/or use of injection device 1. This information is displayed on the display 21 for use by the user of the device. The information may be either processed by supplementary device 2 itself, or may at least partially be provided to another device (e.g. a blood glucose monitoring system or a computing device).

The processor 24 is configured to receive signals form the ONC sensor 30 and to detect when the ONC 12 is not attached to the injection device 10. If the user stores the injection device 10 without the ONC 12 attached, then the needle 17 can become clogged. Therefore, the supplementary device 2 is configured to produce an alarm signal if the processor 24 detects that the ONC 12 has been un-attached for a predetermined length of time following an injection operation. The alarm signal may be sent via the wireless unit 28 to the external user device such that the user can be alerted to the need to replace the ONC 12 even if they have moved away from the supplementary device 2 and injection device 10. Alternatively, or in addition, the alarm signal may comprise the supplementary device 2 displaying words and/or graphics on the display unit 21 or producing sound. The alarm signal may be used to provide a defined alert time for a user to cease use of the device and to use a new device.

Figure 4A:
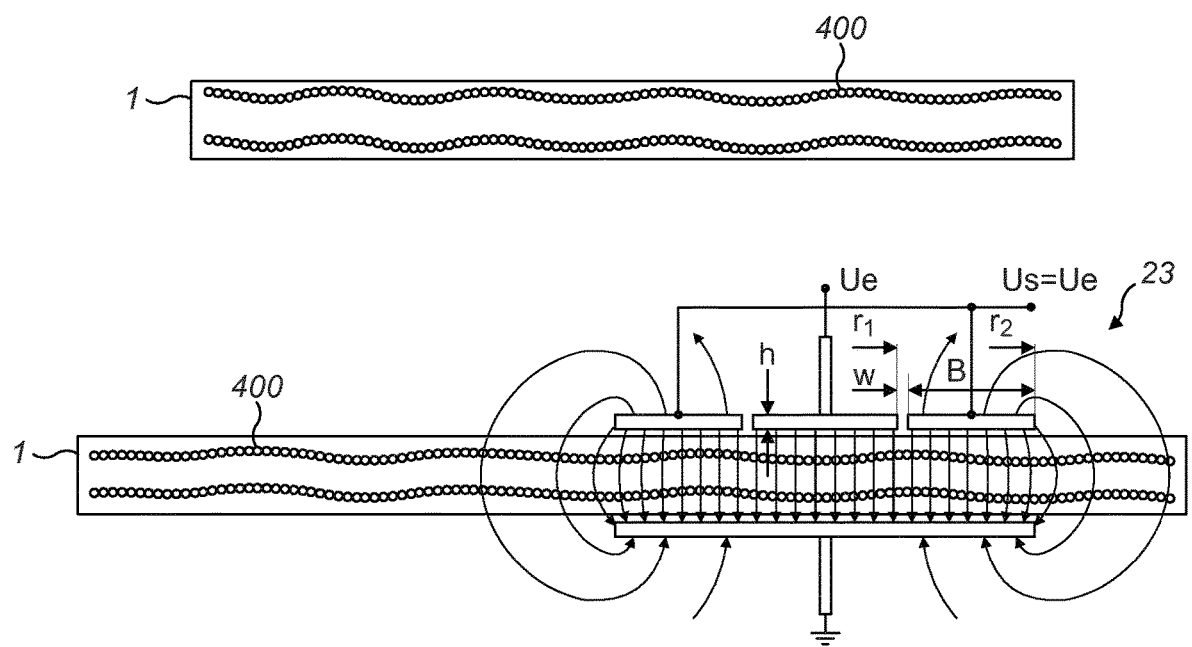
FIG. 4a is a schematic illustration of an injection device and sensor components of the supplementary device for capacitive sensing of the status of the injection device.
Figure 4B:
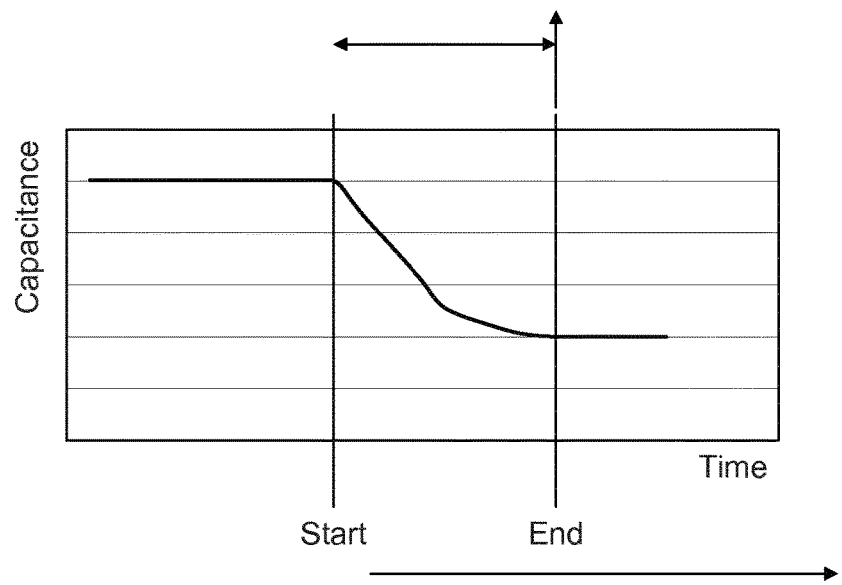
FIG. 4b is a graph illustrating the response of the sensor components shown in FIG. 4a during an injection procedure of the injection device.

In some embodiments, the supplementary device 2 comprises a capacitive sensor 23. Referring now to FIGS. 4a and 4b, the operation of the capacitive sensor 23 will be described in greater detail.

FIG. 4a illustrates shows diagrammatically a cut-away through the injection device 10 when the injection device is in a pre-injection configuration and a post injection configuration (also referred to as pre-activation and post-activation). The injection device 10 comprises a drive spring 400, which is pre-compressed during assembly of the injection device 1. The drive spring 400 is maintained in this pre-compressed state until an injection is performed. When a user triggers an injection operation by pressing dose dispense button 13, the dispense mechanism is released and the drive spring decompresses so as to dispense medicament from the cartridge 18.

Various components of the capacitive sensor 23 are shown schematically in the lower image in FIG. 4a. The capacitive sensor 23 comprises opposing sets of at least one electrically conductive plate. The plates are supported in the housing 20 of the supplementary device 2 so as to be adjacent to the injection device 10 when the supplementary device 2 is attached. The plates may be curved so as to better fit the contours of the supplementary device housing 20. The plates are connected in a circuit so as to form a capacitor. The injection device 10 occupies the space between the plates and functions as the dielectric layer of the capacitor. The capacitive sensor 23 sends signals to the processor 24 via which the processor 24 can determine the effective capacitance.

The upper image in FIG. 4a shows the approximate position of the drive spring 400 before an injection has been performed. The drive spring 400 is compressed, with the coils or windings of the spring being closely spaced or touching. The lower image in FIG. 4a shows the approximate position of the drive spring 400 after the energy stored therein has been released during an injection process. The coils of the drive spring are spaced further apart. In some embodiments the drive spring is metallic.

In an exemplary method of use, the sensor 23 will be set to the capacity of the drive spring 400 prior to injection. The capacity change of the electrically conducting material during injection (the relaxing drive spring 400) can be detected by the sensor 23. The injection will be determined as completed when there is no detected change of the electric field (for example, after a pre-determined lapse time, such as after 5 seconds holding time). The sensor 23 may advantageously be protected against electromagnetic impulses from environmental influences.

FIG. 4b is a graph showing an exemplary relationship between capacitance and charge before, during and after an injection process. Before the injection device 1 is used, the capacitance measured by the capacitive sensor 23 is relatively high, due to the presence of a greater amount of the drive spring 400 in the region between the capacitor plates. The start and end points of the medicament ejection process are shown. During the ejection, the drive spring 400 uncoils such that progressively less of its material is disposed in the region between the capacitor plates. Therefore, the capacitance measured by the capacitive sensor 23 decreases during the injection.

After the injection device 10 has been used, the capacitance measured by the capacitive sensor 23 is relatively low. The sensor 23 may detect a change of the measured capacitance, so the electronic controller knows that the injection is in process. A display may inform a user of the injection being in process. It is intended within the scope of the present disclosure that only hall sensors may be used to determine bung or piston position and so determine when an injection process is at the start and end points. In such an embodiment, two hall sensors may be provided, disposed at the start and end positions of the bung or piston. The bung, or piston may be provided with a magnet for detection by the respective hall sensors at the start and end positions. In alternative embodiments, hall sensors may be used in combination with capacitive sensors, to detect both start and end positions of the injection process, as well as to monitor the progress of the injection process between the start and end positions.

The processor 24 may be configured to determine that an injection has been completed if the capacitance drops from the relatively high value to the relatively low value and remains there for a predetermined time. The processor 24 may be configured to detect the gradual change in measured capacitance in order that the supplementary device 2 can distinguish between an injection process and the supplementary device 2 being removed from the injection device without an injection being performed, in which case a more sudden drop in capacitance would be expected. The capacitive sensor 23 may be shielded so as to protect it from external electromagnetic impulses.

In some embodiments, the supplementary device 2 comprises a Hall sensor 25 (also referred to as a Hall Effect sensor or magnetic sensor). Referring now to FIGS. 5a and 5b, the operation of the Hall sensor 25 will be described in greater detail. In these embodiments a magnet 500 is mounted within the injection device 10 on either the distal or proximal end of the plunger. FIG. 5a illustrates an embodiment in which the magnet 500 is mounted on the distal end of the plunger. The injection device 10 of FIG. 5a is in a pre-activation state. The Hall sensor 25 is positioned within the supplementary device 2 such that it overlays the approximate midpoint of the injection device 10 when the two devices are connected together. This is approximately the longitudinal position that the magnet 500 will occupy at the end of the injection process.

In the pre-activation state, the Hall sensor 25 will detect a very low or no magnetic field due to the relatively large separation between the magnet 500 and Hall sensor 25. During the ejection process, the field detected by the Hall sensor 25 increases. When the injection device 10 is in a post-ejection state, the magnet is located adjacent the Hall sensor 25 and the field detected is relatively high.

FIG. 5b illustrates an alternative arrangement in which a magnet 502 is supported on the proximal end of the plunger. In alternative embodiments, the magnet 502 may be supported on the syringe bung or stopper. The injection device 10 of FIG. 5b is in a post-activation state. The Hall sensor 25 is positioned further towards the proximal end of the supplementary device 2. The choice of whether to use the design in FIG. 5a, or that of FIG. 5b may depend on the size of the supplementary device 2 and its position when mounted to the injection device 10 or on the construction process of the injection device 10.

As with the embodiment described above with reference to FIGS. 4a and 4b, the processor 24 receives the signals from the Hall sensor 25 and can determine whether the injection device 10 is in a pre-injection or post-injection state.

The magnet 500, 502 may be a permanent magnet or alternatively a Ferro magnetic plastic. An advantage of using a plastic magnet, is that it can be moulded to the plunger rod during manufacture. The plastic magnet may need to be magnetized shortly before final assembly of the injection device 10 using a magnetic pulse field.

The processor 24 is configured to receive signals from the capacitive sensor 23 and/or Hall sensor 25 and to infer whether the injection device 10 is in a pre-injection state, a post-injection state or whether an injection process is ongoing. The processor 24 may control the display unit 21 to display different indications to a user depending on the state of the device. This is advantageous as some users may find it difficult to tell whether an injection device 10 has been used or not and also as it aids with the injection operations itself, which some users may find difficult without the presence of the supplementary device 2.

Figure 6A:
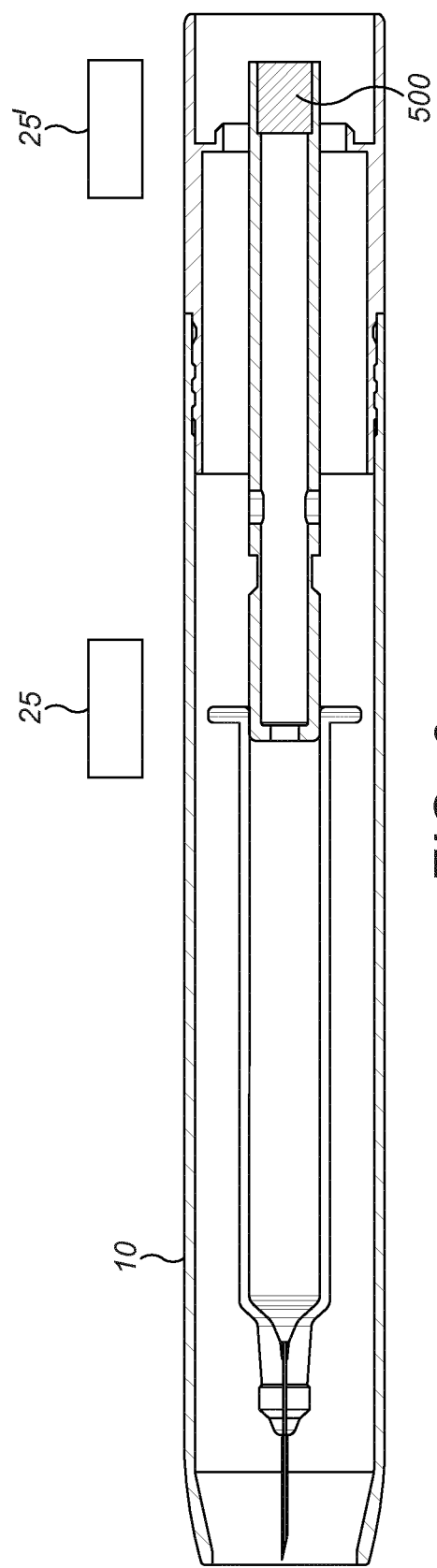
FIGS. 6a, 6b and 7 are further cutaway illustrations of an injection device illustrating the possible position of internal magnets and sensors in three alternative embodiments of the present disclosure.
Figure 6B:
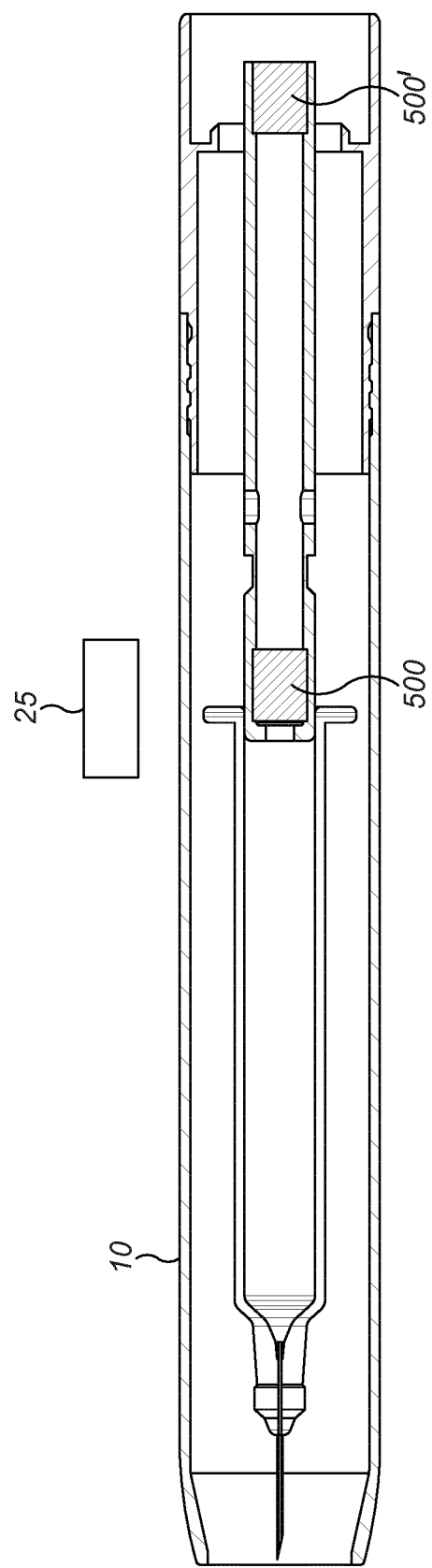

FIGS. 6a and 6b show alternative embodiments of the present disclosure in which one or more Hall sensors are used. Both Figures show the injection device 10 in a pre-activation state. In FIG. 6a, the supplementary device 2 comprises a first Hall sensor 25 and a second Hall sensor 25'. The first and second Hall sensors are arranged in the supplementary device 2 so as to be spaced at different longitudinal positions along the injection device 10. For example, the first Hall sensor 25 may be positioned in the supplementary device 2 so as to be located over the centre region of the injection device 10, while the second Hall sensor 25' may be positioned so as to be located close to the distal end of the injection device 10. The injection device 10 comprises a magnet 500 mounted to the distal end of the plunger. As the magnet 500 moves past the first and second Hall sensors 25, 25', signals are induced in the sensors which can be used to determine the position of the plunger.

When the injection device 10 is activated, the magnet 500 first moves past the second Hall sensor 25'. Signals induced in the second Hall sensor 25' are received by the processor 24 and used to determine that the plunger has begun its movement. Thus the processor 24 is able to determine that an ejection process has begun. As the magnet 500 moves away from the second Hall sensor 25', the signal produced diminishes. As the magnet 500 approaches the first Hall sensor 25, the signal from this sensor increases. As the plunger reaches its final position, the magnet 500 passes underneath the first Hall sensor 25. The first Hall sensor 25 may be positioned such that the magnet 500 stops underneath the sensor 25 or moves completely past the sensor. In either case, the processor 24 is configured to determine from the received signals that the plunger has successfully reached its final position.

In FIG. 6b, the supplementary device 2 comprises a single Hall sensor 25. The injection device 10 comprises a first magnet 500 mounted to the proximal end of the plunger and a second magnet 500' mounted to the distal end of the plunger. The Hall sensor 25 is positioned so that it is located over the central region of the injection device 10 and so that the first magnet 500 is located underneath or near the sensor 25.

When the injection device 10 is activated, the first magnet 500 moves underneath and away from the Hall sensor 25. Signals induced in the Hall sensor 25 are received by the processor 24 and used to determine that the plunger has begun its movement. Thus the processor 24 is able to determine that an ejection process has begun. As the plunger reaches its final position, the second magnet 500' passes underneath the Hall sensor 25. The Hall sensor 25 may be positioned such that the second magnet 500' stops underneath the sensor 25 or moves completely past the sensor. In either case, the processor 24 is configured to determine from the received signals that the plunger has successfully reached its final position.

In the arrangements shown in FIGS. 5a and 5b, the processor can only determine when the plunger arrives at its final position. In the arrangements of FIGS. 6a and 6b, the processor 24 can determine both that the ejection process has successfully begun and that it has completely finished. Having both these determinations allows for better malfunction detection and reporting. This is advantageous, as the injection device 10 itself has no means for detecting malfunctions. Some injection devices have a mechanically operated inspection window, which turns from red to green during ejection, but the remote sensing and detection abilities of the supplementary device 2 provide much more useful information and more accurate and reliable detection of malfunctions.

For example, the processor can determine that the plunger has begun its movement and has continued to move away from its initial position. If, when the injection device 10 is activated, this detection is not made, the processor 24 can determine that the plunger has not moved and that no (or little) medicament has been ejected. If the processor 24 detects that the plunger has begun its movement but does not detect that it has reached its final position, it can be determined that some medicament has been ejected, but not the whole amount. The processor 24 is configured to write information regarding operation of the device and also details of any malfunctions into the log of the supplementary device 2. This can then be reviewed and evaluated, either by the user or the user's health care professional. Being able to determine not only that a malfunction has occurred, but whether any medicament has been ejected or not is potentially important information, as it will likely inform how to proceed with the user's therapy. Informing a user that there has been a device malfunction but that some medicament has been injected helps to prevent accidental overdosing. The supplementary device 2 can additionally sound an alarm and present information to the user via display unit 21. For example, the user can be instructed to seek the advice of their doctor, due to a malfunction of the injection device 10 and also informed as to whether any medicament has been ejected from the device.

In some embodiments the supplementary device 2 comprises either the capacitive sensor 23 or the Hall sensor 25, however in some other embodiments, both sensors may be provided in different parts of the supplementary device 2.

Figure 7:
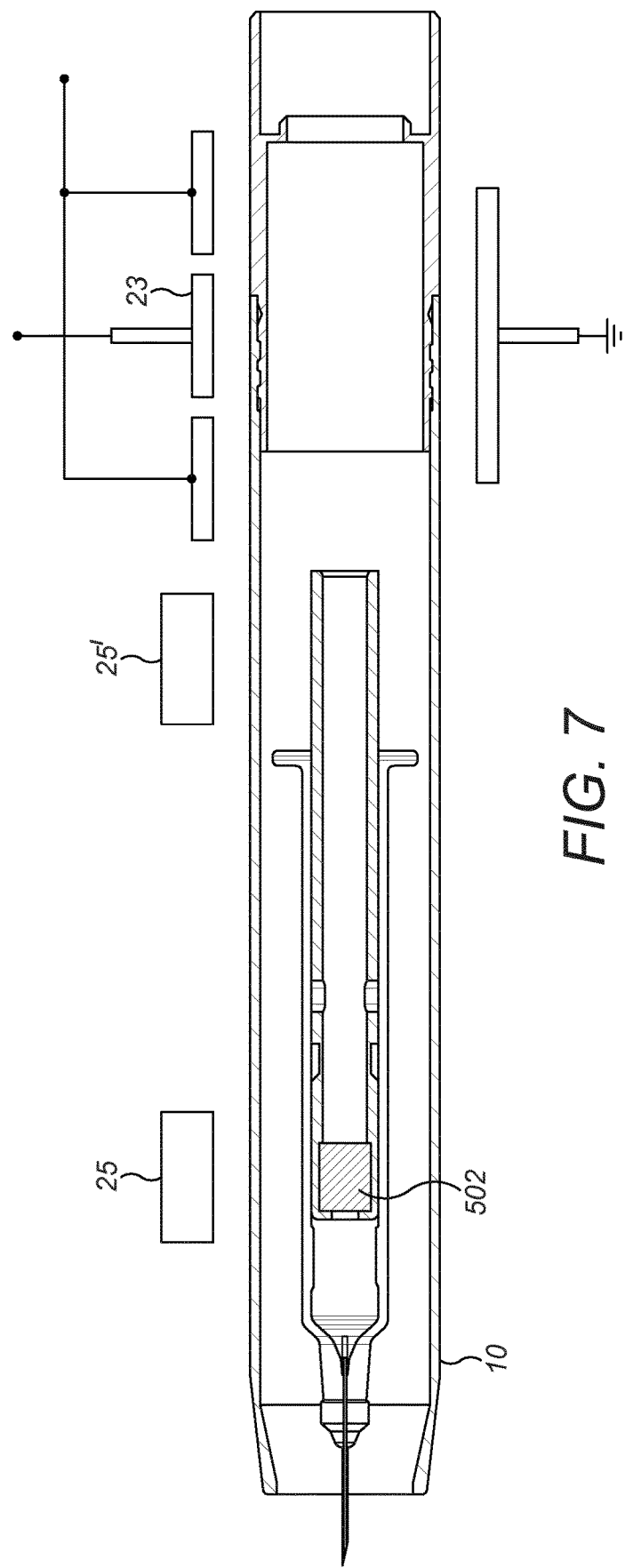

In embodiments where the supplementary device comprises both the capacitive sensor and the Hall sensor, the signals from both of these may be used to detect any mechanical failure of the drug delivery device. FIG. 7 shows an embodiment of the supplementary device 2 comprising both the capacitive sensor 23 and first and second Hall sensors 25, 25'. FIG. 7 illustrates the injection device 10 in a post-activation state. The injection device 10 comprises a magnet 500 disposed on the proximal end of the plunger. As described above with reference to FIG. 6a, the magnet 500 begins underneath or near the second Hall sensor 25' and after activation of the injection device 10 moves away and towards the first Hall sensor 25. When the plunger reaches its final position, the magnet 500 is underneath or near the first Hall sensor 25. The capacitive sensor 23 may be provided at a different location in the supplementary device 2, as shown in FIG. 7. The capacitive sensor 23 is configured to operate as described above with reference to FIGS. 4a and 4b. In this arrangement, the magnet 500 is kept away from the capacitive sensor 23 so as not to affect its readings.

Alternatively, the capacitive sensor 23 may be positioned between the two Hall sensors 25, 25' and software may be used to distinguish the signals due to the un-compressing of the spring 400 and the movement of the magnet 500.

Having both the capacitive sensor 23 and the Hall sensor 25, 25' allows further details on the type of any malfunction to be determined. For example, if the capacitive sensor 23 detects that the drive spring 400 has un-compressed, but the Hall sensors 25, 25' detect that the plunger has not moved, it can be inferred that a mechanical failure relating to the connection between the drive spring and plunger has occurred, either during manufacture or during use. If the Hall sensors 25, 25' detect that the plunger has moved or is not in the correct initial position, but the capacitive sensor 23 detects that the drive spring 400 in still completely compressed, it can be inferred that a mechanical fault has occurred such as that the injection device 10 was incorrectly assembled or does not contain the correct amount of medicament. Suitable alarm signals and information may be generated and displayed by the supplementary device 2 in response to these determinations. The system of FIG. 7 is also able to detect whether medicament has been ejected or not and so prevent accidental overdoses and inform on how to proceed with the user's therapy in the event of a malfunction.

The processor 24 is configured to record a user's injection history. While the injection device 10 may be a single use auto-injector, the supplementary device 2 is reusable, and is configured to be removed from a used injector 10 and attached to a new injector. The processor 24 of the supplementary device 2 has an internal clock in order to create time stamps associated with the injection events. The clock may be a relative clock or an absolute clock. The supplementary device 2 is configured to communicate with an external device through wireless unit 28 and the external device may provide an absolute time.

When the supplementary device 2 is first attached to a new injection device 10, the optical sensor 26 may be activated and the information 100 read. The supplementary device 2 may communicate the information to a user using the display screen 21. When a user performs an injection, this is detected by the capacitive sensor 23 or Hall sensor 25 as described above. A time stamp associated with the injection is then created by the processor 24. The processor 24 also records and associates with the time stamp the type of medicament injected, using the previously read information 100. An external device (not shown) in the user's possession may be registered and associated with the supplementary device 2. The external device may be a mobile computer or smart phone via the wireless unit 28. The mobile computer or smart phone may run a computer program for managing the user's medical records and injection history. The supplementary device 2 is configured to communicate the recorded injection information to the external device.

The processor 24 may be pre-programmed with information relating to the frequency at which the user should perform injections. This programming may take the form of a maximum time between injections or a medical regimen associated with the user of the supplementary device 2. For example, the processor 24 may be pre-programmed with information specifying that the maximum time between injections should be 24 hours. In some other embodiments, the medical regimen may be more detailed, such as to specify specific times of day at which the user is to perform an injection operation using the injection device 10. Alternatively, the processor 24 may be configured to calculate a time at which the user should next perform an injection based on the injection history. For example, the time at which the user should perform the next injection may depend on the amount of medicament previously injected and the frequency of the previous injections. The processor may use the previous injection history to calculate a medical regimen for the user.

When the processor 24 determines that it is time for the user to perform a subsequent injection, it causes a reminder signal to be sent via the wireless unit 28 to the associated external device. The external device may then notify and remind the user that their next injection is due. This is advantageous as the user may not wish to carry the injection device 10 and/or supplementary device 2 with them, but may in any case by carrying a smart phone or similar device. Thus the user can be reminded of the need for a subsequent injection via a separate device which they carry with them. Furthermore, the injection device 10 may need to be kept under specific conditions, such as in a refrigerator or a freezer, such that it is not possible for a user to carry the injection device with them. It is therefore easy for a user to forget about the times at which an injections needs to be performed.

In addition, the processor 24 may be configured to use signals received from the capacitive sensor 23 or Hall sensor 25 to instruct or inform a user regarding 'dwell time'. After a user injects a quantity of medicament into their skin, it is advantageous for the needle to be left in position for a short time (e.g. 5-20 seconds). This may allow the medicament to be diffused away from the injection site. If the needle is removed too soon after an injection, it can result in medicament being expressed from the injection site and the user therefore not receiving a full dose. As previously stated the processor 24 can use the change in signals received from the sensors 23, 25 to determine that an injection is being performed. The processor 24 can infer, when the signals received from the sensors 23, 25 stop changing, that the injection has been completed. This detection can therefore be used as a trigger to display an indication to the user on the display unit 21 instructing them to leave the needle of the injection device 10 in the injection site for a predetermined length of time. The indication may be of any suitable form, for example a timer which counts up or down or a graphic which gets larger/smaller or which fills or un-fills. Other methods of indication may also be used such as sound.

In addition to the components described above, the supplementary device 2 may comprise an ambient light sensor 242. Sometimes the injection device 10 may need to be stored in a refrigerator or a freezer in order to prevent degradation of the medicament over a period of time. The user may attach the supplementary device 2 to an unused injection device 10 after a previous injection, and store the resulting combined system in the fridge/freezer. The ambient light sensor 242 of the supplementary device 2 can be used to detect when the fridge/freezer is opened. This can be used as a trigger for initiating an alarm to remind the user regarding the due time of their next injection. As described above this alarm may take the form of sound emitted by the supplementary device 2, text/graphics displayed on the display unit 21 and/or a reminder send via the wireless unit 28 to the user's smart phone or other external device.

It will be appreciated from the above description that it is important for the correct and accurate functioning of the supplementary device 2 that it is accurately positioned and secured on the injection device 10. For example, it is important that the various sensors such as the ONC sensor, optical sensor 26, hall sensor 25 and/or capacitive sensor 23 are correctly positioned within respect to the components of the injection device 10 they are configured to monitor, detect or otherwise interact with.

In order to enable accurate and secure positioning of the supplementary device 2 on the injector device 10, the supplementary device may include one or more particular positioning features. The injector device 10 may also comprise complimentary features configured to engage with those positioning features of the supplementary device 2.

Figure 8:
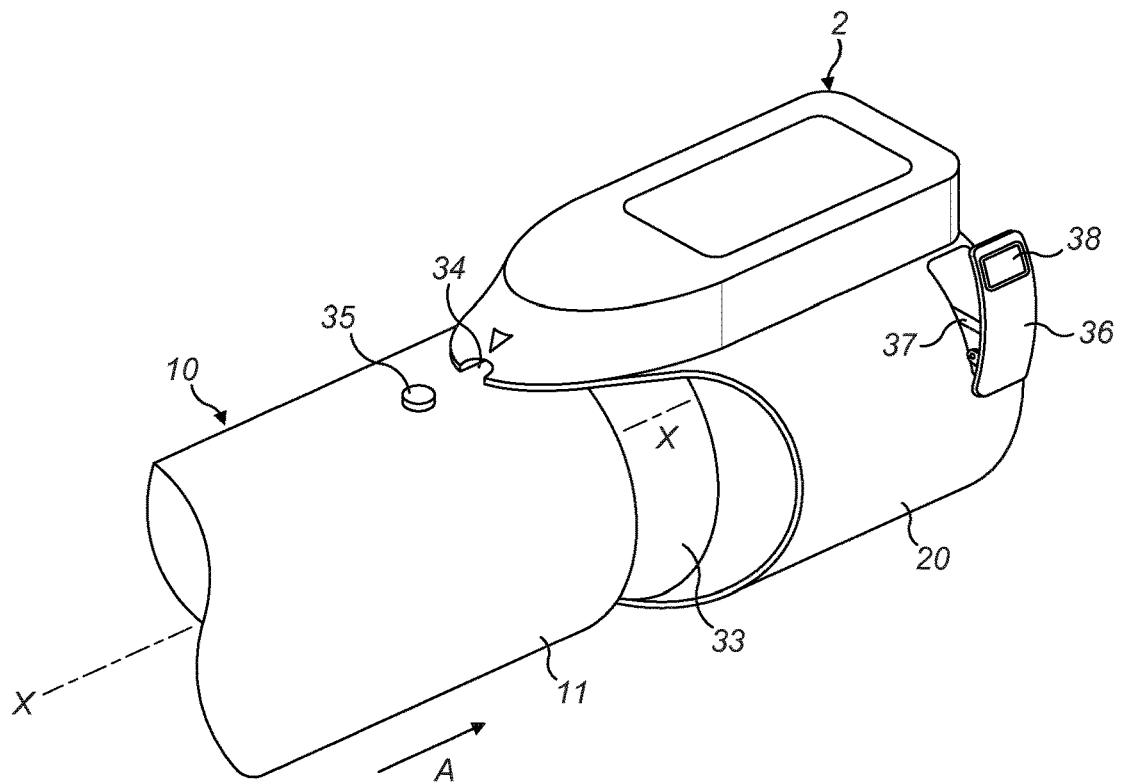
FIG. 8 is a perspective view of an injection device during insertion into a supplementary device of the present disclosure.
Figure 9:
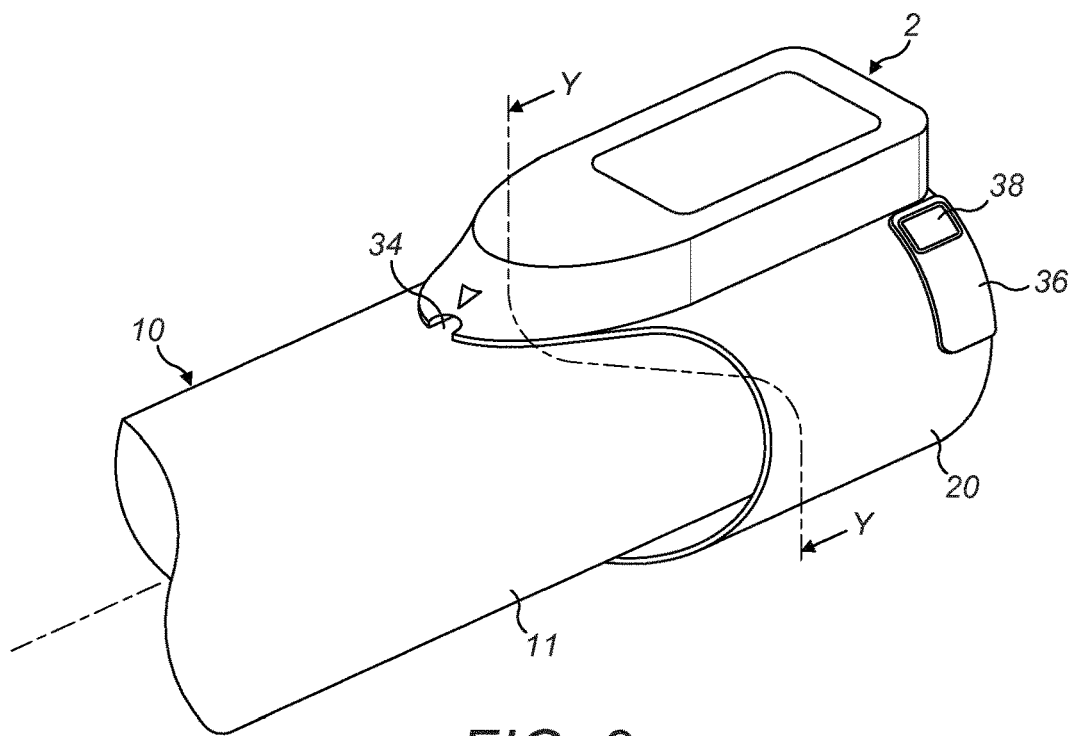
FIG. 9 illustrates the injection device and supplementary device of FIG. 8 once the injection device is fully inserted.
Figure 10:
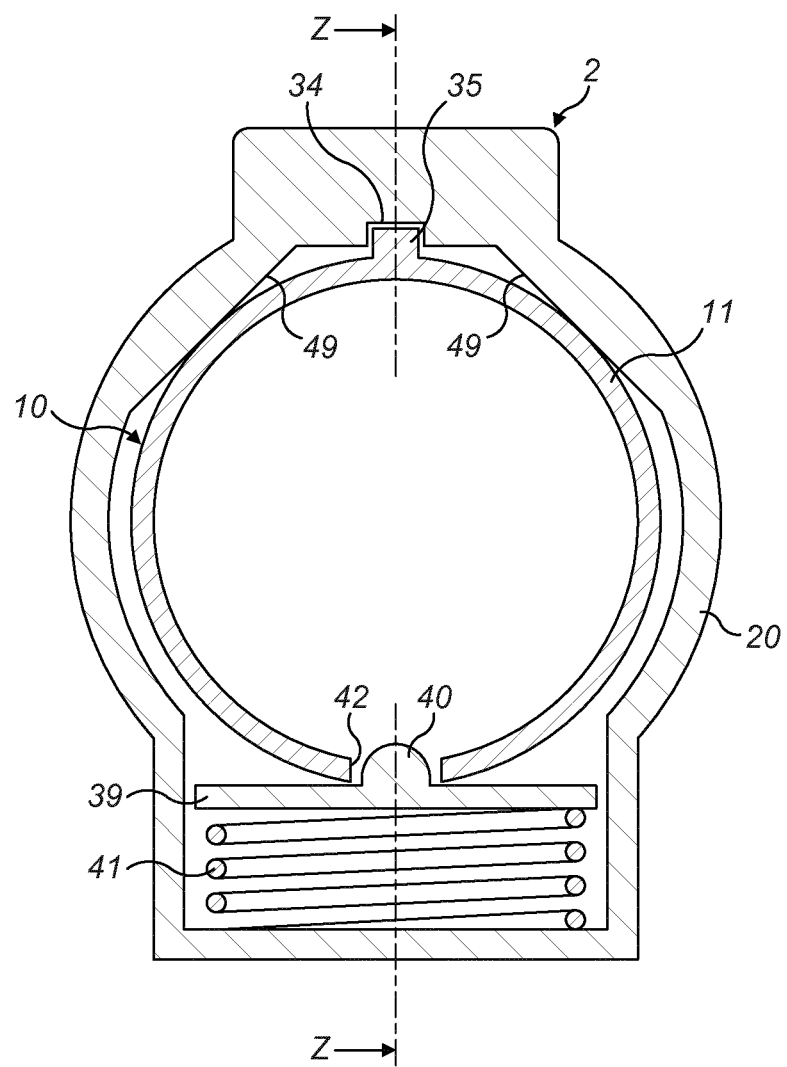
FIG. 10 illustrate a schematic cross-sectional view through the injection device and supplementary injection device of FIG. 9, along the line Y-Y.
Figure 11:
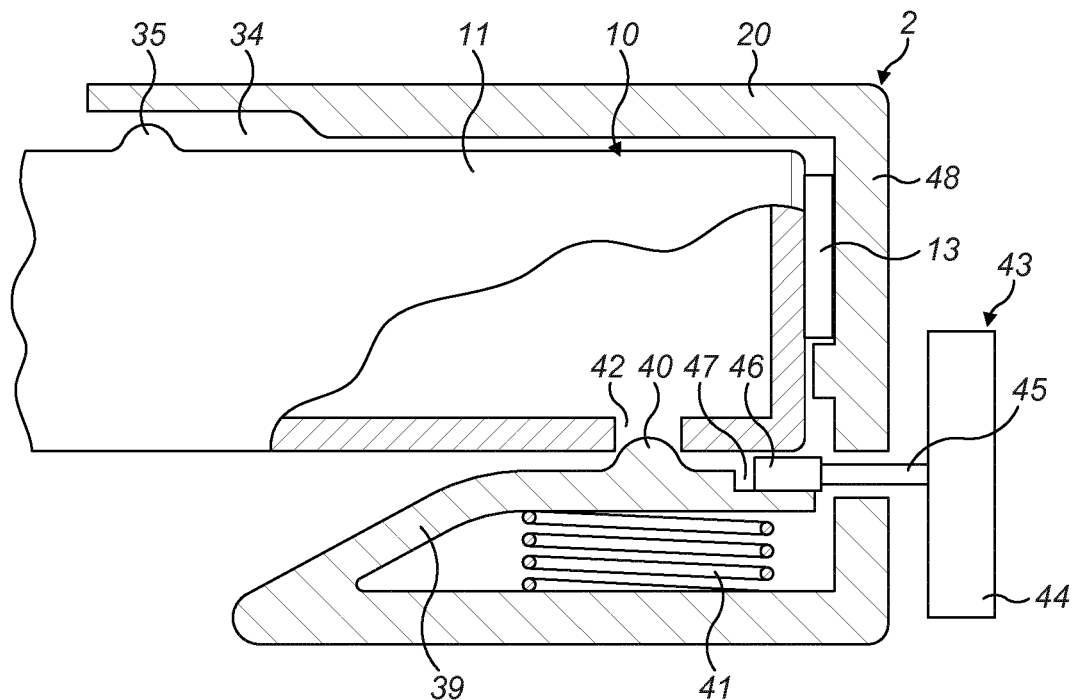
FIG. 11 illustrates a schematic cross-sectional view through the injection device and supplementary injection device of FIGS. 9 and 10, along the line Z-Z of FIG. 10.
Figure 12:
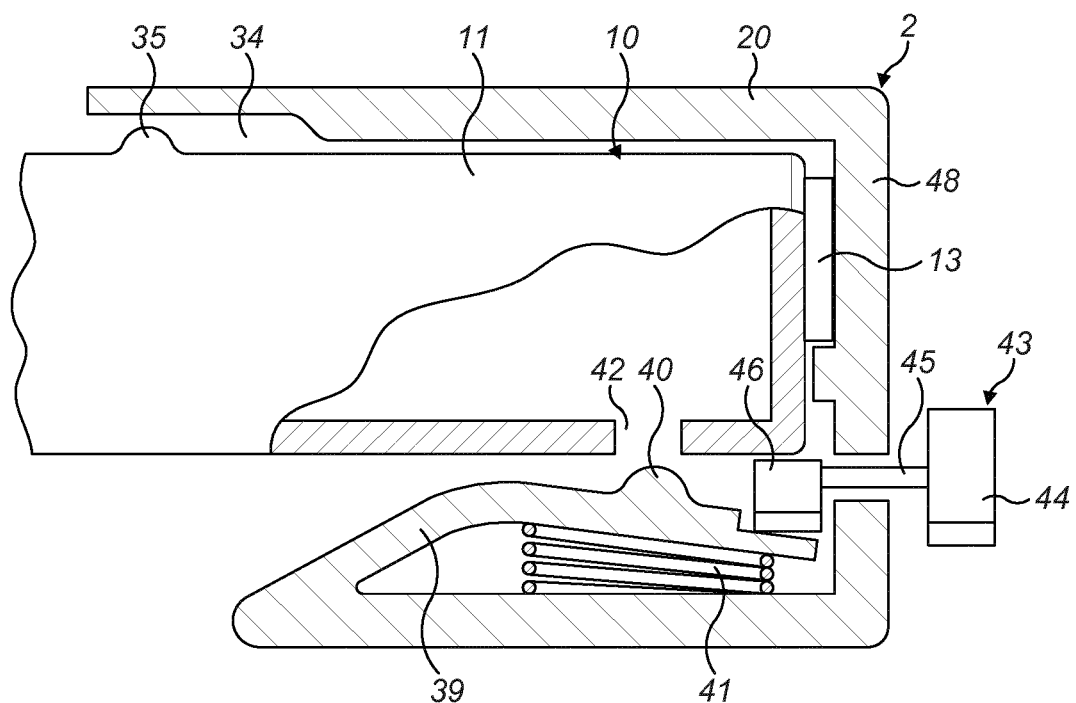
FIG. 12 illustrates a schematic cross-sectional view similar to that of FIG. 11 with the supplementary device in a release configuration.

FIGS. 8 and 9 show the supplementary device 2 and illustrate such positioning features. FIG. 8 shows the supplementary device 2 during insertion of the injector device 10 but before the injector device 10 is fully inserted. FIG. 9 shows the injector device 10 fully inserted and secured within the supplementary device 2. FIG. 10 shows a cross-sectional view along the line Y-Y in FIG. 9, with the injector device 10 fully inserted and secured within the supplementary device 2. FIG. 11 shows a cross-sectional view along the line Z-Z in FIG. 10. FIG. 12 shows a cross-sectional view similar to that of FIG. 11, but with the supplementary device 2 in a release configuration.

The housing 20 of the supplementary device 2 defines a channel. Within the scope of this disclosure, the channel may be open along one side or part thereof, or may have a wall around its entire perimeter or circumference. In the exemplary embodiment, the channel comprises a generally cylindrical aperture 33 configured to receive the injector device 10. The injector device 10 is a substantially cylindrical elongate body having a longitudinal axis X-X as shown in FIG. 8. The injector device 10 is inserted into the cylindrical aperture 33 of the housing 20 by sliding the injector device 10 in the axial direction shown by arrow 'A' in FIG. 8.

The housing 20 includes a first alignment feature comprising an elongate slot 34 formed on an inside wall of the cylindrical aperture 33 at an upper side of the housing 20. The slot 34 is open at a front end of the housing 20 which faces the proximal end P of the injector device 10. This can also be seen in the cross-sectional views of FIGS. 11 and 12. The outer housing 11 of the injector device 10 includes a projection 35 at an upper side thereof. When the injector device 10 is inserted into the supplementary device 2, the projection 35 slides into the slot 34. It will be appreciated that, by means of the first alignment feature, the injector device 10 can only be inserted into the supplementary device 2 when the slot 34 and projection 35 are aligned, ensuring correct rotational position of the injector device 10 relative to the supplementary device 2 about the axis X-X. Also, once the injector device 10 is inserted into the supplementary device 2, relative rotational movement of the injector device 10 relative to the supplementary device 2 is prevented by means of the first alignment feature. The first alignment feature thereby serves as an "anti-roll" feature.

Although the channel in the housing 20 is described above as comprising a generally cylindrical aperture 33 configured to receive the injector device 10, the present disclosure is not intended to be limited to this configuration of an entirely rounded or cylindrical aperture 33. In an alternative embodiment, the channel or aperture 33 defined by the housing may include flat portions to locate against the elongate body of the injection device 10. These features of such an embodiment are shown in FIG. 10, as opposing slanted flat surfaces 49. Each surface is advantageously equally spaced from the centre line (shown by line Z-Z of FIG. 10) of the supplementary device 2. Each surface is advantageously angled by the same degree away either side of a vertical line through the supplementary device (again, shown by line Z-Z in FIG. 10). Such flat surfaces may provide reference surfaces, as a third alignment feature, against which the elongate body of the injection device 10 abuts. These may advantageously guide the elongate body of the injection device 10 to be centrally aligned within supplementary device 2. This may advantageously prevent axial misalignment of the injection device 10 and supplementary device 2 which may otherwise occur if both the outer housing 11 of the injection device 10 and the aperture 33 of the supplementary device 2 were entirely circular, due to manufacturing tolerances.

The housing 20 further comprises a second alignment feature. In the embodiment shown, the second alignment feature comprises an axial locating mechanism to secure the injector device 10 in place within the housing 20 once it has been fully inserted and is at the correct position axially relative to the housing 20. The locating mechanism is disposed at a lower side of the housing, substantially opposite the first alignment feature, and is shown in FIGS. 10 to 12. The locating mechanism comprises a securing member which, in the exemplary embodiment, comprises a sprung plate 39. The sprung plate 39 has a boss 40 extending upwardly from the plate 39. A spring 41 is disposed between the underside of the spring plate 39 and the inside wall of the housing 20. The spring 41 biases the spring plate 39 in a direction away from the adjacent wall of the housing 20 and towards the injection device 20. As shown in FIGS. 11 and 12, the sprung plate 39 comprise a curved arm which may be formed integrally with the housing, 20, or may be connected to the housing by mechanical fastening or bonding. The curved arm 39 may be biased in a direction towards the injector device 10 by virtue of the deflection and material resilience of the curved arm. In such an embodiment, the spring 41 may be provided to provide additional biasing force to the sprung plate 39. Alternatively the spring 41 may be omitted.

The outer housing 11 of the injector device 10 includes a recess 42 in a lower side thereof. The recess 42 is disposed facing the boss 40 of the sprung plate 39 and is configured to receive the boss 40. When the injector device 10 has been fully inserted into the housing 20 and is at the correct position in an axial direction relative to the housing 20, the boss 40 locates in the recess 42 and is held in the recess by the force of the spring 41 and/or the resilience of the arm 39. The injector device 10 is thereby prevented from movement in the direction of the axis X-X of the injector device by means of the second alignment feature. It will be appreciated that, in the embodiment shown, the second alignment feature also serves to prevent rotation of the injector device 10 relative to the housing 20 about the axis X-X, so acts as a secondary anti-rotation feature. It will also be appreciated that, in the embodiment shown in FIG. 10, the force of the spring 41 and/or resilience of the arm 39 urges the injector device 10 upwards against the centrally inwardly angled flat reference surfaces 49 and so helps to centrally align the injector device 10 within the supplementary device 2.

The axial locating mechanism includes a release member. In the exemplary embodiment, the release member comprises a release lever 43. The release lever 43 is configured such that rotation of the release lever 43 deflects the sprung plate 39 away from the injector device 10 to disengage the boss 40 from the recess 42. The release lever 43 comprises a handle 44 on the outside of the housing 20, a shaft 45 and a paddle 46 projecting radially from the shaft at the opposite end thereof to the handle 44. The release lever 43 is rotatable between a rest position, as shown in FIG. 11, and a release position, as shown in FIG. 12. In the rest position, the paddle 46 sits within a cavity 47 in the sprung plate 39 so that the sprung plate 39 is disposed with the boss 40 received in the recess 42. When the handle 44 is turned through 90 degrees into the release position, the paddle 46 pushes the sprung plate 39 downwards so that the boss 40 is disengaged from the recess 42. Although the exemplary configuration of release member 43 is shown and described as a release lever 43, this disclosure is not limited to this particular configuration and other configurations of release member or other release mechanism are intended within the scope of the disclosure. For example, the release member may comprise a slider with a projection that engages the sprung plate 39.

The housing 20 additionally includes a locking mechanism to lock the injector device 10 in place once fully received in the housing 20. The locking mechanism comprises a locking lever 36 pivotable between an unlocked position shown in FIG. 8 and a locked position shown in FIG. 9. The lever 36 includes a pin 37 projecting from an inner face of the lever 36 which is received in a corresponding hole (not shown) in the outer housing 11 of the injector device 10 when the lever 36 is in the locked position.

In the embodiment shown, the lever 36 includes a status indicator 38 to indicate to a user whether the lever 36 is fully engaged in the locked position. This may help ensure the user only uses the injector device 10 when it is correctly assembled and ready for use. Different embodiments of status indicator 38 are envisaged within the scope of this disclosure. The indicator 38 may be an LED within the locking lever. For example, the LED may illuminate red when unlocked and green when locked. Alternatively, the LED may be off when unlocked and on when locked, or vice versa. The LED may be activated on or off, or between colours by electrical contact with the housing 20 when in the locked position. Such contact may be via the pin 37 or by contact with another part of the lever 36. Alternatively, the indicator may be mechanically actuated when the lever 36 is moved between the locked and unlocked positions. For example, a coloured plate may be moved into and out of view in a display window of the indicator 38.

The injector device 10 and/or the supplementary device 2 may be configured to be inoperable until the lever 36 is moved into the locked position. For example, the pin 37 may provide an electrical contact with a control circuit or switch of the injector device 10 and/or the supplementary device 2 so that operation is only possible once the lever 36 is in the locked position. In addition, the supplementary device 2 may be configured such that movement of the lever 36 into the locked or unlocked position may trigger one or more of the actions of the supplementary device 2 described previously. For example, moving the lever 36 into the locked position may turn on the supplementary device 2. Conversely, moving the lever 36 into the unlocked position may turn off the supplementary device 2. Also, moving the lever 36 into the locked or unlocked position may trigger a pairing or connection function, or initiate transmission of information.

The locking lever 36 may be configured to provide an audible feedback when it is securely located in the locked position. For example, the locking lever 36 may engage with a click or snap. This may give a user both tactile and audible feedback that the locking mechanism is properly engaged and so an injection process can be started.

It will be appreciated that various configurations of supplementary device 2 are envisaged within the scope of this disclosure which enable user-operation of the injection device 10. For example, in one embodiment, such as that shown schematically in FIG. 2, the dose dispense button 13 protrudes through an opening in an end of the housing 20. In an alternative embodiment, such as that shown in FIGS. 8 to 12, and particularly FIGS. 11 and 12, an end wall 48 of the housing 20 may be deflectable so a user can push the end wall to depress the dose dispense button. In a further alternative embodiment (not shown), the end wall 48 of the housing 20 may include a sliding button which is in abutment with the dose dispense button 13. The sliding button of the housing 20 may therefore be depressed to depress the dose dispense button 13.

Engagement and disengagement of the injector device 10 and supplementary device 2 will now be described. A user inserts the injection device 10 into the aperture 33 of the housing 20 in the direction of arrow A in FIG. 8. The user aligns the projection 35 with the slot 34 and continues to insert the injection device 10 into the housing 20 such that the projection 35 is received in the slot 34.

The user continues to push the injection device 10 into the housing 20 until fully received therein, as shown in FIGS. 9 to 11. In this position, the boss 40 locates in the recess 42 to secure the injector device 10 in the fully-inserted position. A user then moves the locking lever 36 from the unlocked position to the locked position to lock the injection device 10 in place in the housing 20. As discussed above, this movement to the locked position may also actuate or prime the injector device, or render the injector device in an operable state. Once the locked position, the status indicator 38 indicates to the user that the injector device 10 and supplementary device 2 are ready for use. The user may then operate the injection device to administer the medicament dose.

Once the medicament delivery process is complete, and the supplementary device 2 is to be removed from the injection device 10, a user moves the locking lever 36 from the locked position to the unlocked position. The status indicator may indicate to the user that the supplementary device 2 is unlocked from the injection device 10. A user then turns the handle 44 of the release lever 43, which causes the paddle 46 to push the sprung plate 39 downwards away from the injection device 10. This causes the boss 40 to disengage from the recess 42. The injection device 10 is then free to be slid out of the aperture 33 in the housing 20. The injection device 10 can then be stored for reuse, recycled or disposed of in a suitable manner. The supplementary device 2 may then be stored for re-use with another injection device 10 at a later time.

It will be appreciated that various alternatives to the exemplary embodiments shown and described above are intended to fall within the scope of this disclosure, defined by the claims hereafter. In one such embodiment, the first alignment feature may be of an alternative configuration to the elongate slot 34 and projection 35 shown above. For example, the aperture 33 in the housing may be of a non-round shape, and the outer housing 11 of the injection device 10 may be of a corresponding shape. Therefore, the injection device 10 may only be receivable in the housing 20 in a particular rotational position relative to the axis X-X. Alternatively, the housing may have one or more flat or shaped alignment surfaces and the outer housing 11 may have correspondingly shaped alignment surfaces for abutment with the alignment surfaces of the housing 20. Again, such a configuration of housing 20 would ensure that the injection device 10 may only be receivable in the housing 20 in a particular rotational position relative to the axis X-X. Also, all such alternative embodiments of first alignment feature would prevent rotational movement of the injector device 10 relative to the supplementary device 2 about the axis X-X and thereby serve as an "anti-roll" feature.

Although the first alignment feature is shown as a slot 34 in the housing 20, which is configured to receive a projection 35 on the injection device 10, the present disclosure is not limited to this configuration and these features may be reversed. For example, the first alignment feature may comprise a projection formed on the inner face of the aperture 33 of the housing 20. Such projection may be configured to engage with a slot formed in the outer housing 11 of the injection device 10.

Although the second alignment feature is shown as a slot boss 40 on the sprung plate 39, which is received in a recess 42 in the outer housing 22 of the injection device, the present disclosure is not limited to this configuration and these features may be reversed. For example, the second a projection may comprise a recess formed in the sprung plate. Such a recess may be configured to receive a boss formed on the outer housing 11 of the injection device 10.

Furthermore, although the embodiment shown comprises both first and second alignment features, the present disclosure is not limited to this configuration and the supplementary device may alternatively comprise only one alignment feature. Such single alignment feature may preferably be configured to prevent rotational and axial movement of the supplementary device relative to the injection device.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyhepta ¬-decanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia. Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the APIs, substances, formulations, apparatuses, methods, systems and embodiments described herein may be made without departing from the full scope and spirit of the present invention, which encompass such modifications and any and all equivalents thereof

The invention claimed is:

1. A supplementary device configured to be releasably attached to a drug delivery device, the supplementary device comprising:
a housing having a channel configured to slidably receive the drug delivery device;
a first alignment feature to provide a specific alignment of the supplementary device relative to the drug delivery device and restrict rotational movement of the supplementary device around the drug delivery device; and
a second alignment feature to prevent sliding movement of the supplementary device relative to the drug delivery device when the supplementary device is attached to the drug delivery device,
wherein the second alignment feature comprises:
a moveable securing member biased towards the drug delivery device; and
a release member being moveable to be urged against the securing member, the release member being moveable between a rest position in which the securing member is permitted to engage the drug delivery device, and a release position in which the securing member is moved out of engagement with the drug delivery device.

2. The supplementary device according to claim 1, wherein the first alignment feature is configured to engage with a cooperating feature of the drug delivery device and permit sliding movement of the drug delivery device within the channel.

3. The supplementary device according to claim 2, wherein the first alignment feature comprises a slot formed in the housing, the slot configured to receive a projection formed on the drug delivery device.

4. The supplementary device according to claim 1, wherein the securing member comprises a boss configured to be received in a recess formed in the drug delivery device.

5. The supplementary device according to claim 1, further comprising a biasing member configured to bias the securing member towards the drug delivery device.

6. The supplementary device according to claim 1, wherein the securing member is integrally formed with the housing.

7. The supplementary device according to claim 1, wherein the release member comprises a release lever rotatable between the rest position in which the securing member is permitted to engage the drug delivery device, and the release position in which the securing member is moved out of engagement with the drug delivery device.

8. The supplementary device according to claim 7, wherein the release lever comprises a shaft and a radial projection from the shaft, the release lever configured to engage with the securing member.

9. The supplementary device according to claim 1, further comprising a locking mechanism including an actuator moveable between a locked position and an unlocked position, wherein the locking mechanism is operable to releasably lock the supplementary device to the drug delivery device.

10. The supplementary device according to claim 9, wherein the actuator includes a visual indicator to indicate that the actuator is in one of the locked position or the unlocked position.

11. The supplementary device according to claim 9, wherein the actuator is configured to render the supplementary device operable when the supplementary device is in the locked position and inoperable when the supplementary device is in the unlocked position.

12. The supplementary device according to claim 9, wherein the actuator is configured to trigger a function of the supplementary device when the actuator is moved to one or both of the locked position or the unlocked position.

13. The supplementary device according to claim 1, wherein the release member is moveable relative to the securing member to move the securing member out of engagement with the drug delivery device.

14. The supplementary device according to claim 1, wherein the release member is slidable relative to the securing member to move the securing member out of engagement with the drug delivery device.

15. The supplementary device according to claim 1, wherein the first alignment feature and the second alignment feature of the supplementary device respectively cooperate with corresponding alignment features of the drug delivery device.

16. A system comprising:
a drug delivery device; and
a supplementary device configured to be releasably attached to the drug delivery device, the supplementary device comprising:

a housing having a channel configured to slidably receive the drug delivery device;

a first alignment feature to provide a specific alignment of the supplementary device relative to the drug delivery device and restrict rotational movement of the supplementary device around the drug delivery device; and a second alignment feature to prevent sliding movement of the supplementary device relative to the drug delivery device when the supplementary device is attached to the drug delivery device, wherein the second alignment feature comprises:

a moveable securing member biased towards the drug delivery device; and a release member being moveable to be urged against the securing member, the release member being moveable between a rest position in which the securing member is permitted to engage the drug delivery device, and a release position in which the securing member is moved out of engagement with the drug delivery device.

17. The system according to claim 16, wherein the drug delivery device comprises a reservoir of liquid medicament.

18. A method of operating a supplementary device configured to be releasably attached to a drug delivery device, the supplementary device comprising a housing having a channel, a first alignment feature, and a second alignment feature comprising a moveable securing member biased towards the drug delivery device and a release member, the method comprising:

sliding the drug delivery device into the channel in the housing of the supplementary device;

releasably attaching the supplementary device to the drug delivery device such that the first alignment feature engages with the drug delivery device to provide a specific alignment of the supplementary device relative to the drug delivery device and restrict rotational movement of the supplementary device around the drug delivery device, and the second alignment feature engages with the drug delivery device to prevent sliding movement of the supplementary device relative to the drug delivery device when the supplementary device is attached to the drug delivery device; and moving the release member to urge the release member against the securing member, wherein moving the release member comprises moving the release member between a rest position in which the securing member is permitted to engage the drug delivery device, and a release position in which the securing member is moved out of engagement with the drug delivery device.

* * * * *